(12) United States Patent
Green et al.

(10) Patent No.: US 9,079,838 B2
(45) Date of Patent: Jul. 14, 2015

(54) ORTHO-PHENYLPHENOL COMPOUNDS

(75) Inventors: George David Green, Cary, IL (US); Raymond John Swedo, Mount Prospect, IL (US)

(73) Assignee: Dow Global Technologies LLC, Midland, MI (US)

( * ) Notice: Subject to any disclaimer, the term of this patent is extended or adjusted under 35 U.S.C. 154(b) by 102 days.

(21) Appl. No.: 14/115,480

(22) PCT Filed: May 7, 2012

(86) PCT No.: PCT/US2012/036767
§ 371 (c)(1),
(2), (4) Date: Nov. 4, 2013

(87) PCT Pub. No.: WO2012/154668
PCT Pub. Date: Nov. 15, 2012

(65) Prior Publication Data
US 2014/0081051 A1      Mar. 20, 2014

Related U.S. Application Data
(60) Provisional application No. 61/483,867, filed on May 9, 2011.

(51) Int. Cl.
| C07C 43/205 | (2006.01) |
| C07C 69/78 | (2006.01) |
| C10L 1/185 | (2006.01) |
| C10L 1/00 | (2006.01) |

(52) U.S. Cl.
CPC .............. *C07C 43/2055* (2013.01); *C07C 69/78* (2013.01); *C10L 1/003* (2013.01); *C10L 1/1852* (2013.01)

(58) Field of Classification Search
None
See application file for complete search history.

(56) References Cited

U.S. PATENT DOCUMENTS
| 5,981,283 | A | 11/1999 | Anderson, II et al. |
| 7,858,373 | B2 | 12/2010 | Banavali et al. |
| 2011/0289831 | A1 | 12/2011 | Green |
| 2012/0090225 | A1 | 4/2012 | Green |

FOREIGN PATENT DOCUMENTS
| EP | 512404 | A1 | 11/1992 |
| WO | 2012154646 | A1 | 11/2012 |

OTHER PUBLICATIONS
Database CAPLUS on STN, Acc. No. 1935:22825, Vernon et al., Journal of the American Chemical Society (1935), 57, pp. 527-528 (abstract).*
Database CAPLUS in STN, Acc. No. 1975:5559, Bielowski et al., Zeszyty Naukowe Politechniki Slaskiej, Chemia (1973), 64, pp. 129-134 (abstract).*
Musser, David M. et al., "The Selective Hydrogenation of Derivatives of Naphthalene and Diphenyl", The Laboratory of Organic Chemistry of the University of Wisconsin, Nov. 29, 1937. pp. 664-669. vol. 60.
Deadly, et al., "Preparation of some chromans from 1,3-diaryloxypropanes", Journal of the Chemical Society, Oct. 1965, pp. 5718-5724.
Bielowski, Piotr, et al., "Preparation and Some Properties ester sulfonate alkyl diphenyl", Scientific Papers of Silesian University of Technology,: Chemistry z 64, No. col. 382., pp. 129-134, 1973.

* cited by examiner

*Primary Examiner* — Brian J Davis
(74) *Attorney, Agent, or Firm* — Kenneth Crimaldi

(57) ABSTRACT

A compound having formula (I),

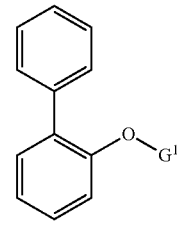

(I)

wherein $G^1$ represents a $C_4$-$C_{22}$ alkyl or alkenyl group, a $C_8$-$C_{20}$ aralkyl group or formula (II)

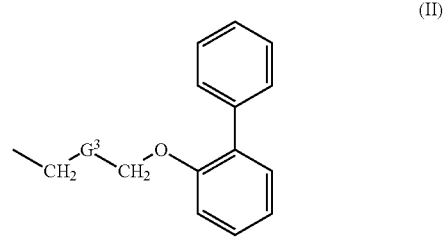

(II)

wherein $G^3$ is a difunctional $C_2$-$C_{18}$ alkyl or alkenyl group, a difunctional $C_6$-$C_{20}$ aryl group or $G^3$ is absent; provided that $G^1$ is not 2-butyl, n-hexyl, n-octyl, n-dodecyl, n-hexadecyl or 2-phenylethyl.

3 Claims, No Drawings

ORTHO-PHENYLPHENOL COMPOUNDS

This invention relates to new compounds useful in a method for marking liquid hydrocarbons and other fuels and oils.

Marking of petroleum hydrocarbons and other fuels and oils with various kinds of chemical markers is well known in the art. A variety of compounds have been used for this purpose, as well as numerous techniques for detection of the markers, e.g., absorption spectroscopy and mass spectrometry. For example, U.S. Pat. No. 7,858,373 discloses the use of a variety of organic compounds for use in marking liquid hydrocarbons and other fuels and oils. However, there is always a need for additional marker compounds for these products. Combinations of markers can be used as digital marking systems, with the ratios of amounts forming a code for the marked product. Additional compounds useful as fuel and lubricant markers would be desirable to maximize the available codes. The problem addressed by this invention is to find additional markers useful for marking liquid hydrocarbons and other fuels and oils.

STATEMENT OF INVENTION

The present invention provides a compound having formula (I),

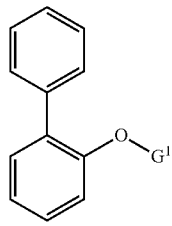

wherein $G^1$ represents a $C_4$-$C_{22}$ alkyl or alkenyl group, a $C_8$-$C_{20}$ aralkyl group or formula (II)

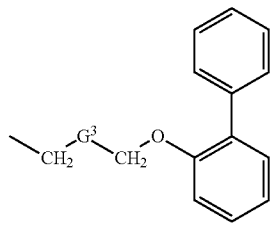

wherein $G^3$ is a difunctional $C_2$-$C_{18}$ alkyl or alkenyl group, a difunctional $C_6$-$C_{20}$ aryl group or $G^3$ is absent; provided that $G^1$ is not 2-butyl, n-hexyl, n-octyl, n-dodecyl, n-hexadecyl or 2-phenylethyl.

DETAILED DESCRIPTION

Percentages are weight percentages (wt %) and temperatures are in ° C., unless specified otherwise. Concentrations are expressed either in parts per million ("ppm") calculated on a weight/weight basis, or on a weight/volume basis (mg/L); preferably on a weight/volume basis. The term "petroleum hydrocarbon" refers to products having a predominantly hydrocarbon composition, although they may contain minor amounts of oxygen, nitrogen, sulfur or phosphorus; petroleum hydrocarbons include crude oils as well as products derived from petroleum refining processes; they include, for example, crude oil, lubricating oil, hydraulic fluid, brake fluid, gasoline, diesel fuel, kerosene, jet fuel and heating oil. Marker compounds of this invention can be added to a petroleum hydrocarbon or a liquid biologically derived fuel; examples of the latter are biodiesel fuel, ethanol, butanol, ethyl tert-butyl ether or mixtures thereof. A substance is considered a liquid if it is in the liquid state at 20° C. A biodiesel fuel is a biologically derived fuel containing a mixture of fatty acid alkyl esters, especially methyl esters. Biodiesel fuel typically is produced by transesterification of either virgin or recycled vegetable oils, although animal fats may also be used. An ethanol fuel is any fuel containing ethanol, in pure form, or mixed with petroleum hydrocarbons, e.g., "gasohol." An "alkyl" group is a substituted or unsubstituted hydrocarbyl group having from one to twenty-two carbon atoms in a linear or branched arrangement. Substitution on alkyl groups of one or more hydroxy or alkoxy groups is permitted. Preferably, alkyl groups are saturated and unsubstituted. An "aryl" group is a substituent derived from an aromatic hydrocarbon compound. An aryl group has a total of from six to twenty ring atoms, unless otherwise specified, and has one or more rings which are separate or fused. Substitution on aryl groups of one or more alkyl or alkoxy groups is permitted. An "aralkyl" group is an "alkyl" group substituted by an "aryl" group, e.g., benzyl or 2-phenylethyl. Preferably, the compounds of this invention contain elements in their naturally occurring isotopic proportions.

A "difunctional group" is a substituent group having two points of attachment, e.g., one example of a difunctional alkyl group would be —$(CH_2)_n$—, where n is an integer having the specified range; an example of a difunctional aryl group would be a phenylene radical (i.e., benzene attached at two positions, e.g., 1,4-phenylene radical), or biphenyl attached at two positions.

Preferably, the compound of formula (I) is represented by formula (III)

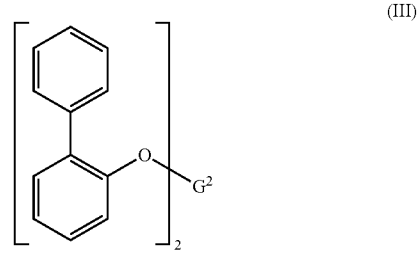

wherein $G^2$ is —$CH_2$-$G^3$-$CH_2$—. In comparing formula (III) to formula (I), it is clear that to arrive at formula (III), $G^1$ in formula (I) would be

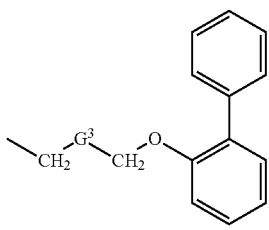

wherein the substituent depicted by formula (IV) is attached to the oxygen atom shown in formula (I). Preferably, $G^3$ is $-(CH_2)_n-$ or $-Ar-$, where n is an integer from 2 to 20 and Ar is a difunctional $C_6-C_{20}$ aryl group. Preferably, n is from 2 to 12, preferably from 2 to 10, preferably from 2 to 8, preferably from 2 to 6, preferably from 4 to 6. Preferably, Ar is a difunctional $C_6-C_{14}$ aryl group, preferably $C_6-C_{12}$.

Preferably, $G^1$ represents a $C_{14}$ or $C_{18}$ alkyl group, a $C_4-C_{12}$ branched primary alkyl group, a $C_4-C_{18}$ alkenyl group or a $C_8-C_{14}$ aralkyl group, provided that $G^1$ is not 2-phenylethyl; preferably a $C_{14}$ alkyl group, a $C_5-C_{12}$ branched primary alkyl group, a $C_5-C_{16}$ alkenyl group or a $C_8-C_{12}$ aralkyl group, provided that $G^1$ is not 2-phenylethyl. Especially preferred $C_8-C_{12}$ aralkyl groups include benzyl groups substituted by one or more methyl and/or methoxy groups. Preferably, $G^1$ represents a $C_{14}-C_{22}$ alkyl group, preferably $C_{14}$ or $C_{18}$, preferably $C_{14}$. Preferably, $G^1$ represents a branched $C_4-C_{22}$ alkyl group attached to the oxygen atom in formula (I) via a primary carbon atom, e.g., isobutyl, isoamyl, isohexyl, 2-ethylhexyl. Preferably, $G^1$ represents a $C_5-C_{22}$ secondary alkyl group, e.g., 2-pentyl, preferably a $C_6-C_{18}$ secondary alkyl group, preferably a $C_6-C_{14}$ secondary alkyl group.

In using the compounds of this invention as markers, preferably the minimum amount of each compound added to a liquid to be marked is at least 0.01 ppm, preferably at least 0.02 ppm, preferably at least 0.05 ppm, preferably at least 0.1 ppm, preferably at least 0.2 ppm. Preferably, the maximum amount of each marker is 50 ppm, preferably 20 ppm, preferably 15 ppm, preferably 10 ppm, preferably 5 ppm, preferably 2 ppm, preferably 1 ppm, preferably 0.5 ppm. Preferably, the maximum total amount of marker compounds is 100 ppm, preferably 70 ppm, preferably 50 ppm, preferably 30 ppm, preferably 20 ppm, preferably 15 ppm, preferably 12 ppm, preferably 10 ppm, preferably 8 ppm, preferably 6 ppm, preferably 4 ppm, preferably 3 ppm, preferably 2 ppm, preferably 1 ppm. Preferably, a marker compound is not detectible by visual means in the marked petroleum hydrocarbon or liquid biologically derived fuel, i.e., it is not possible to determine by unaided visual observation of color or other characteristics that it contains a marker compound. Preferably, a marker compound is one that does not occur normally in the petroleum hydrocarbon or liquid biologically derived fuel to which it is added, either as a constituent of the petroleum hydrocarbon or liquid biologically derived fuel itself, or as an additive used therein.

Preferably, the marker compounds have a log P value of at least 3, where P is the 1-octanol/water partition coefficient. Preferably, the marker compounds have a log P of at least 4, preferably at least 5. Log P values which have not been experimentally determined and reported in the literature can be estimated using the method disclosed in Meylan, W. M & Howard, P. H., *J. Pharm. Sci.*, vol. 84, pp. 83-92 (1995). Preferably the petroleum hydrocarbon or liquid biologically derived fuel is a petroleum hydrocarbon, biodiesel fuel or ethanol fuel; preferably a petroleum hydrocarbon or biodiesel fuel; preferably a petroleum hydrocarbon; preferably crude oil, gasoline, diesel fuel, kerosene, jet fuel or heating oil; preferably gasoline.

Preferably, the marker compounds are detected by at least partially separating them from constituents of the petroleum hydrocarbon or liquid biologically derived fuel using a chromatographic technique, e.g., gas chromatography, liquid chromatography, thin-layer chromatography, paper chromatography, adsorption chromatography, affinity chromatography, capillary electrophoresis, ion exchange and molecular exclusion chromatography. Chromatography is followed by at least one of: (i) mass spectral analysis, and (ii) FTIR. Identities of the marker compounds preferably are determined by mass spectral analysis. Preferably, mass spectral analysis is used to detect the marker compounds in the petroleum hydrocarbon or liquid biologically derived fuel without performing any separation. Alternatively, marker compounds may be concentrated prior to analysis, e.g., by distilling some of the more volatile components of a petroleum hydrocarbon or liquid biologically derived fuel.

Preferably, more than one marker compound is present. Use of multiple marker compounds facilitates incorporation into the petroleum hydrocarbon or liquid biologically derived fuel of coded information that may be used to identify the origin and other characteristics of the petroleum hydrocarbon or liquid biologically derived fuel. The code comprises the identities and relative amounts, e.g., fixed integer ratios, of the marker compounds. One, two, three or more marker compounds may be used to form the code. Marker compounds according to this invention may be combined with markers of other types, e.g., markers detected by absorption spectrometry, including those disclosed in U.S. Pat. No. 6,811,575; U.S. Pat. App. Pub. No. 2004/0250469 and EP App. Pub. No. 1,479,749. Marker compounds are placed in the petroleum hydrocarbon or liquid biologically derived fuel directly, or alternatively, placed in an additives package containing other compounds, e.g., antiwear additives for lubricants, detergents for gasoline, etc., and the additives package is added to the petroleum hydrocarbon or liquid biologically derived fuel.

The compounds of this invention may be prepared by methods known in the art, e.g., condensation of o-phenylphenol with organic halides in the presence of base. For example, o-phenylphenol may be allowed to react with an aliphatic dihalide according to the following equation.

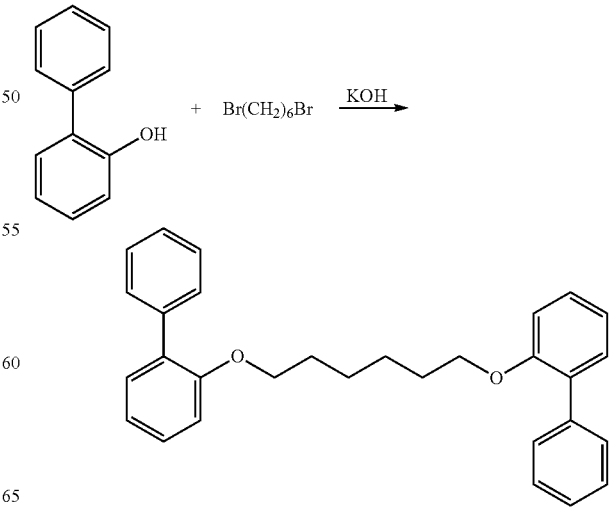

Reaction of o-phenylphenol with aliphatic or aralkyl monohalides also leads to compounds within the scope of the present invention.

EXAMPLES

Example 1

Preparation of 1,3-bis(([1,1'-biphenyl]-2-yloxy)-methyl)benzene

A 100 mL 3-neck flask was equipped with a magnetic stirrer, a reflux condenser, a nitrogen blanket, and a heating mantle with a temperature controller and a thermocouple. The flask was charged with o-phenylphenol (6.83 grams, 0.04 moles), with KOH (2.63 grams, 0.04 moles), and with 25 mL of DMSO. The mixture was stirred at about 35° C. for about ¾ hour, then a solution of α,α'-dichloro-m-xylene (3.52 grams, 0.02 moles) in 5 mL of DMSO was added to the dark solution over about 25 minutes. After the addition, the reaction mixture was heated at 50° C. for about 3 hours, and then it was poured into about 400 mL of water. A sticky white solid separated. The mixture was slurried with about 75 mL of diethyl ether; the solids dissolved. The mixture was transferred to a separatory funnel, and the layers were separated. The aqueous layer was extracted with 2×75 mL of diethyl ether. The ether layers were combined and were washed with 1×75 mL of saturated aqueous sodium chloride solution, and then they were dried over anhydrous magnesium sulfate. After filtration, the ether was removed by rotary evaporation at a bath temperature of about 60° C./P=3.4 kPa to give 8.42 grams of clear, viscous brown oil. Yield=95%. Structure was confirmed by IR, GC/MS, and $^1$H- and $^{13}$C-NMR analyses.

Examples 2-4

The identical procedure was followed with other benzyl halide reactants. In each case, the $^1$H, $^{13}$C-NMR, IR, GC/MS were consistent with the identity and purity of the product.

4,4'-bis(([1,1'-biphenyl]-2-yloxy)methyl)-1,1'-biphenyl; MP=149-151° C., 89.9% yield, 100% GPC purity, soluble at 10% in NMP at −10° C.

1,2-bis(([1,1'-biphenyl]-2-yloxy)-methyl)benzene; isolated as an oil, 93% yield, 99% GPC purity, soluble at 10% in AROMATIC 200, tetralin, NMP, DMAc, dipropylene glycol dimethyl ether at −10° C.

1,4-bis(([1,1'-biphenyl]-2-yloxy)-methyl)benzene; MP=140-142° C., 89.5% yield, 100% GPC purity, soluble at 10% in NMP at −10° C.

Example 5

Preparation of 2-(hexadecyloxy)-1,1'-biphenyl

A 100 mL 3-neck flask was equipped with a magnetic stirrer, a reflux condenser, a nitrogen blanket, and a heating mantle with a temperature controller and a thermocouple. The flask was charged with o-phenylphenol (3.42 grams, 0.02 moles), with KOH pellets (1.37 grams, 0.02 moles, 85%), and with 15 mL of DMSO. The mixture was stirred at 100° C. under nitrogen until all of the KOH had dissolved (about 2 hours). The dark solution was cooled to 70° C., then the 1-chlorohexadecane (5.22 grams, 0.02 moles) was then added all at once. An exotherm to about 80° C. was observed. The reaction mixture was then stirred at 75° C. for about 7.5 hours, then it was poured into about 500 mL of water; solids separated. After stirring at room temperature for about 2 hours, the mixture was filtered. The solids were washed on the filter with a little water, then they were air dried to give 7.58 grams of waxy white solid. The yield was 96%; mp=35-37° C. Structure was confirmed by IR, GC/MS, and $^1$H- and $^{13}$C-NMR analyses.

Examples 6-8

The identical procedure was followed with other alkyl halide reactants. In each case, the $^1$H, $^{13}$C-NMR, IR, GC/MS were consistent with the identity and purity of the product.

2-(dodecyloxy)-1,1'-biphenyl; isolated as an oil, 89% yield, 98% GPC purity, soluble at 10% in AROMATIC 200, tetralin, dipropylene glycol dimethyl ether at −10° C.

2-(tetradecyloxy)-1,1'-biphenyl; MP=27-29° C., 90% yield, 99% GPC purity, soluble at 7.5% in tetralin at −10° C.

2-(octadecyloxy)-1,1'-biphenyl; MP=42-45° C., 94% yield, 90% GPC purity, soluble at <5% in tetralin at −10° C.

Example 9

Preparation of 1,6-bis([1,1'-biphenyl]-2-yloxy)hexane

A 250 mL 3-neck flask was equipped with a magnetic stirrer, a reflux condenser, a nitrogen blanket, and a heating mantle with a temperature controller and a thermocouple. The flask was charged with o-phenylphenol (6.81 grams, 0.04 moles), with KOH pellets (2.64 grams, 0.04 moles, 85%), and with 50 mL of DMSO. The mixture was stirred at about 35° C. for about 1½ hours, then 1,6-dibromohexane (4.88 grams, 0.02 moles) was added in one portion. The reaction mixture was stirred at about 75° C. for about 2 hours, then it was poured into about 500 mL of water. A milky white suspension formed. The mixture was slurried with about 100 mL of diethyl ether, then it was transferred to a separatory funnel. The layers were separated, and the aqueous layer was extracted with 5×100 mL of diethyl ether. The ether layers were combined, and were washed with 1×100 mL of water and with 1×100 mL of saturated aqueous sodium chloride. After drying the ether solution over anhydrous magnesium sulfate, the solution was filtered, and the solvent was removed by rotary evaporation at a bath temperature of about 60° C./P=3.4 kPa. The yield of product was 7.06 grams (84%) as a white solid having mp=92-95° C. Structure was confirmed by IR, GC/MS, and $^1$H- and $^{13}$C-NMR analyses.

Examples 10-12

The identical procedure was followed with other α,ω-dihaloalkane reactants. Where GPC purity is provided, the $^1$H, $^{13}$C-NMR, IR, GC/MS were consistent with the identity and purity of the product.

1,3-bis([1,1'-biphenyl]-2-yloxy)propane; not isolated, 55% GPC purity.

1,4-bis([1,1'-biphenyl]-2-yloxy)butane; MP=62-67° C., 94% yield, 88% GPC purity, soluble at 10% in NMP, DMAc, dipropylene glycol dimethyl ether at −10° C.

1,2-bis([1,1'-biphenyl]-2-yloxy)ethane (identified in reaction mix by GC/MS)

Example 13

Preparation of [1,1'-biphenyl]-2-yl benzoate

A 250 mL round bottom flask equipped with efficient magnetic stirring was charged with o-phenylphenol (17.0 g, 0.1 mol), toluene (100 mL) and triethylamine (11.1 g, 0.11 mol, 10% excess). Benzoyl chloride (14.7 g, 0.105 mol, 5% excess) was added portionwise over 15 minutes while using an ice bath to help maintain the temperature below 30° C. The initially clear reaction mixture became a white slurry during the acid chloride addition. After stirring at room temperature for an additional 2.5 hours, the slurry was filtered and the clear organic layer was stripped on a rotary evaporator at 60° C./P=3.4 kPa. The light yellow oil crystallized upon cooling. The crude product was recrystallized from a mixture of hexane (100 mL)/toluene (20 mL) yielding 25.7 g (93.8%) white crystals. The structure was confined using $^{13}C$ and $^{1}H$ NMR, IR and GC/MS.

GC/MS Linearity, Repeatability, and Accuracy Data for Ex. 9 Product

Method Evaluation for Ex. 9 product in methylene chloride (DCM):

| Stock | Stock(mg/ml) | SubStock(ug/ml) |
|---|---|---|
| Ex. 9 product | 0.43 | 5.359 |

10.7 mg in 25 ml DCM, 0.313 ml Stock in 25 ml DCM

| Standard | 1 | 2 | 3 | 4 | 5 |
|---|---|---|---|---|---|
| Substock | 200 ul | 400 ul | 600 ul | 800 ul | 1,000 ul |
| DMBBP(ug/L) | 107 | 214 | 322 | 429 | 536 |

Linearity and Accuracy:

| Standard | Conc(ppb) | Area | Conc.(ppb) | % Recovery |
|---|---|---|---|---|
| 1 | 107 | 9269 | 108.8 | 101.5 |
| 1 | 107 | 9199 | 108.1 | 100.9 |
| 2 | 214 | 20070 | 212.9 | 99.3 |
| 2 | 214 | 20940 | 221.3 | 103.2 |
| 3 | 322 | 31420 | 322.3 | 100.2 |
| 3 | 322 | 30863 | 316.9 | 98.6 |
| 4 | 429 | 41890 | 423.2 | 98.7 |
| 4 | 429 | 41064 | 415.2 | 96.9 |
| 5 | 536 | 55118 | 550.7 | 102.8 |
| 5 | 536 | | | |

Repeatability and Accuracy: These are the data for Ex. 9 product

| | Concentration | | | | | |
|---|---|---|---|---|---|---|
| | 214 ppb | | | 536 ppb | | |
| Rep | Area | Conc. (ppb) | % Recovery | Area | Conc. (ppb) | % Recovery |
| 1 | 18458 | 197.4 | 92.1 | 52024 | 520.8 | 97.2 |
| 2 | 18480 | 197.6 | 92.2 | 51175 | 512.7 | 95.7 |
| 3 | 18985 | 202.4 | 94.4 | 51443 | 515.2 | 96.2 |
| 4 | 19118 | 203.7 | 95.0 | 51266 | 513.5 | 95.8 |
| 5 | 18398 | 196.8 | 91.8 | 51288 | 513.7 | 95.9 |
| 6 | 18474 | 197.5 | 92.1 | 51160 | 512.5 | 95.6 |
| Avg. | 18652 | 199.2 | 92.9 | 51393 | 514.8 | 96.1 |
| Std Dev | 314 | 3.02 | 1.41 | 325 | 3.14 | 0.59 |
| RSD | 1.68 | 1.52 | 1.52 | 0.63 | 0.61 | 0.61 |

Note:
1 SIM: 422 + 170
2 Solvent: Dichloromethane (DCM)

GC/MS Detection of Ex. 13 Product: A 500 ppb solution was prepared in dichloromethane. A 2 uL injection of this mixture resulted in an easily detectable peak giving an area count of 156313 using the combined ion responses at 105 and 274 amu.

GC Parameters for Detection:

| | Parameters |
|---|---|
| Column | Varian VF1701 |
| Maxium Temp (C.) | 300 |
| Length (m) | 30 |
| Flow Rate (ml/min) | 0.9 |
| Initial Temp (C.) | 100 |
| Hold (min) | 3 |
| Rate1 (C./min) | 10 |
| Final Temp1 (C.) | 290 |
| Hold (min) | 20 |

Solubility of Ex. 13 Product: A solution (10% w/w) in AROMATIC 200 was prepared at room temperature. The clear solution was placed in a −11° C. freezer for 2 weeks. No visibly detectable crystallization occurred.

The invention claimed is:

1. A compound having formula (I),

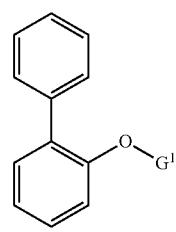

(I)

wherein $G^1$ represents a formula (II)

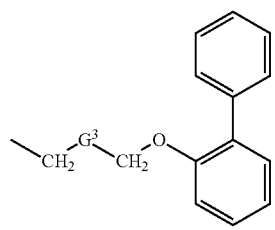

(II)

wherein $G^3$ is —$(CH_2)_n$— wherein n is an integer from 4 to 6 or a difunctional $C_6$-$C_{20}$ aryl group.

2. The compound of claim 1 in which $G^1$ represents formula (II) and $G^3$ is a difunctional $C_6$-$C_{14}$ aryl group.

3. The compound of claim 2 in which $G^3$ is a difunctional $C_6$-$C_{12}$ aryl group.

* * * * *